United States Patent [19]

Kuramoto et al.

[11] Patent Number: 4,792,912
[45] Date of Patent: Dec. 20, 1988

[54] SYSTEM FOR ESTIMATING THERMAL STRESS OF PRESSURE PARTS

[75] Inventors: Atsushi Kuramoto, Kure; Yukio Fukayama, Hiroshima; Shigeyoshi Kawano, Kure, all of Japan

[73] Assignee: Babcock-Hitachi Kabushiki Kaisha, Tokyo, Japan

[21] Appl. No.: 726,645

[22] Filed: Apr. 24, 1985

[30] Foreign Application Priority Data

Apr. 24, 1984 [JP] Japan ................... 59-81158

[51] Int. Cl.⁴ .............................................. F01J 5/00
[52] U.S. Cl. ........................... 364/557; 364/558; 374/137; 290/40 R; 60/646
[58] Field of Search ............ 364/557, 558, 497, 510, 364/508; 60/646; 340/57; 290/40 R; 374/46, 124, 137

[56] References Cited

U.S. PATENT DOCUMENTS

| | | | |
|---|---|---|---|
| 4,173,891 | 11/1979 | Johnson | 364/497 |
| 4,228,359 | 10/1980 | Matsumoto et al. | 290/40 R |
| 4,364,676 | 12/1982 | Oja et al. | 364/557 |
| 4,393,365 | 7/1983 | Kondo et al. | 340/57 |
| 4,535,593 | 8/1985 | Sakka | 60/646 |

FOREIGN PATENT DOCUMENTS 0026673 4/1981 European Pat. Off. ............ 374/124

*Primary Examiner*—Parshotam S. Lall
*Assistant Examiner*—V. N. Trans
*Attorney, Agent, or Firm*—Fay, Sharpe, Beall, Fagan, Minnich & McKee

[57] ABSTRACT

Thermal stress of a metal portion of a pressure-tight tube is calculated on the basis of calculated values of a temperature distribution calculator for calculating the distribution of temperature at positions equidistantly arranged in a direction of the thickness of the aforesaid tube on the basis of measured values of metal portion of the aforesaid tube, whereby the thermal stress being changed momently is accurately measured and monitored. Further, there is provided a calculation cycle setter for presetting calculation cycles on the basis of measured values of the fluid temperature in the aforesaid tube. The calculation cycles are made short when fluctuations in the measured values of the fluid temperature are large, while, the calculation cycles are made long when fluctuations in the measured values of the fluid temperature are small.

10 Claims, 3 Drawing Sheets

SYSTEM FOR ESTIMATING THERMAL STRESS OF PRESSURE PARTS

BACKGROUND OF THE INVENTION

1. Field of the Invention

This invention relates to a system for estimating thermal stress, wherein the thermal stress generated in pressure parts of thermal equipment such as a boiler is monitored, while a load is controlled to the optimal value.

2. Detailed Description of the Prior Art

At the time of the start, stop or change in the load of a boiler, fluid temperature greatly changes, whereby a temperature difference between the metal part and the internal fluid becomes larger.

Because of this, thermal stress is generated in the pressure part of the boiler, particularly, in a nozzle corner portion of a thick-wall pressure part such as an outlet header of a secondary superheater, high thermal stress is generated, whereby the life of the thick wall pressure parts is shortened by low cycle fatigue.

On the other hand, even during steady operation, the internal pressure stress due to the internal fluid, causes creep damage of thick-wall pressure parts that accumulates.

The thermal stress generated in a thick-wall tube of the pressure part of the boiler has heretofore been estimated from the distribution of temperature in the direction of the wall thickness, and the following are known as the methods of estimating the distribution of temperature.

(1) The first one of the methods is based on an actual measured value of internal fluid temperature for estimating an inner surface metal temperature, and on a perfect thermal insulation condition for estimating an outer surface metal temperature. Using these conditions, non-stationary heat transfer equations are solved to obtain the temperature distribution of the metal part in the direction of thickness, and the thermal stress is calculated. However, in this method, it is necessary to estimate the heat transfer coefficient between the internal fluid and the inner metal surface exactly. Usually, a constant value is used as the heat transfer coefficient because of the difficulty of the exact estimation. Then the estimation accuracy of the temperature distribution in the metal is not satisfactory.

(2) Temperatures are measured on two points close to the outer surface and the inner surface of the thick-wall metal part, and the distribution of temperature in a direction of the wall thickness is approximated by a straight line between these two points to thereby measure the generated stress.

The following disadvantages are presented by the method wherein the distribution of temperature in the direction of the wall thickness is measured, which has heretofore been practised, and the generated stress is estimated on the basis of the distribution of temperature thus measured.

(1) The boundary condition of the outer surface of the metal is assumed to be for a perfect thermal insulation condition, however, in practice, there is radiation, though it is small.

Further, it is unreasonable to contemplate improving the accuracy of measuring the generated stress, because the coefficient of heat-transfer for the boundary condition of the inner surface of the metal greatly changes due to the flow rate of the internal fluid and/or evaporation conditions.

(2) When the distribution of temperature in the direction of the wall thickness is approximated by the straight line, the generated stress is underestimated to be lower than the actually generated stress.

A temperature distribution calculation cycle and a stress calculation cycle have heretofore been conducted at predetermined intervals of time irrespective of changes in the internal fluid temperature, when the stress generated in the thick-wall tube of the pressure part of the boiler is estimated from the distribution of temperature in the direction of the wall thickness.

The following disadvantages are presented by the method of estimating the generated stress, wherein the calculation cycles have been conducted at the predetermined intervals of time as described above.

(1) All of the operating conditions of a plant are assumed and the calculation cycles are determined so that the generated stress can be accurately estimated under the state where the change is largest.

In other words, even at the time of steady operation where fluctuations in the fluid temperature are small, the generated stress is estimated in the same calculation cycles as those at the time of the start, stop or the load change, whereby the accuracy is in error at the time of the steady operation.

(2) In general, at the time of the start, stop or the load change in a power plant, a computer load is severe with a control computer. Calculation of the thermal stress at predetermined time intervals of time irrespective of the state of the plant is regarded as one of causes of increasing the load imposed on the computer.

SUMMARY OF THE INVENTION

The present invention has been developed to obviate the above-described disadvantages of the prior art and has as its object the provision of a system for estimating the thermal stress, wherein the distribution of temperature in the direction of the wall thickness of a pressure part used in thermal equipment such as a boiler is estimated with high accuracy, so that the generated stress can be measured at a value close to the actual state.

Another object of the present invention is to provide a system for measuring the thermal stress, wherein the calculation cycles are made different with the time of either the load change of the heating device such as the boiler or the steady operation, so that the generated stress can be measured at a value close to the actual state.

To this end, the present invention contemplates to provide a system for measuring thermal stress of a pressure-tight tube, including: a temperature distribution calculator for calculating distribution of temperature at positions equidistantly arranged in a direction of the thickness of the metal pressure part on the basis of measured values on a metal portion thereof; and a thermal stress calculator for calculating thermal stress of the metal portion.

It is preferable that the present invention be of such an arrangement that there is provided a calculation cycle setter for presetting the calculation cycles on the basis of measured values of temperature of the internal fluid, the calculation cycles being made short at the time where fluctuations in the measured value of the fluid temperature are large, and the calculation cycles being made long at the time of the steady operation where fluctuations in the measured value of the fluid temperature are small.

The present invention is preferably applicable to pressure parts incorporated in a boiler, a heating furnace, a cracker or the like, wherein fluid is heated. Description will hereunder be given of a boiler embodying the present invention.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION

Figure 1:
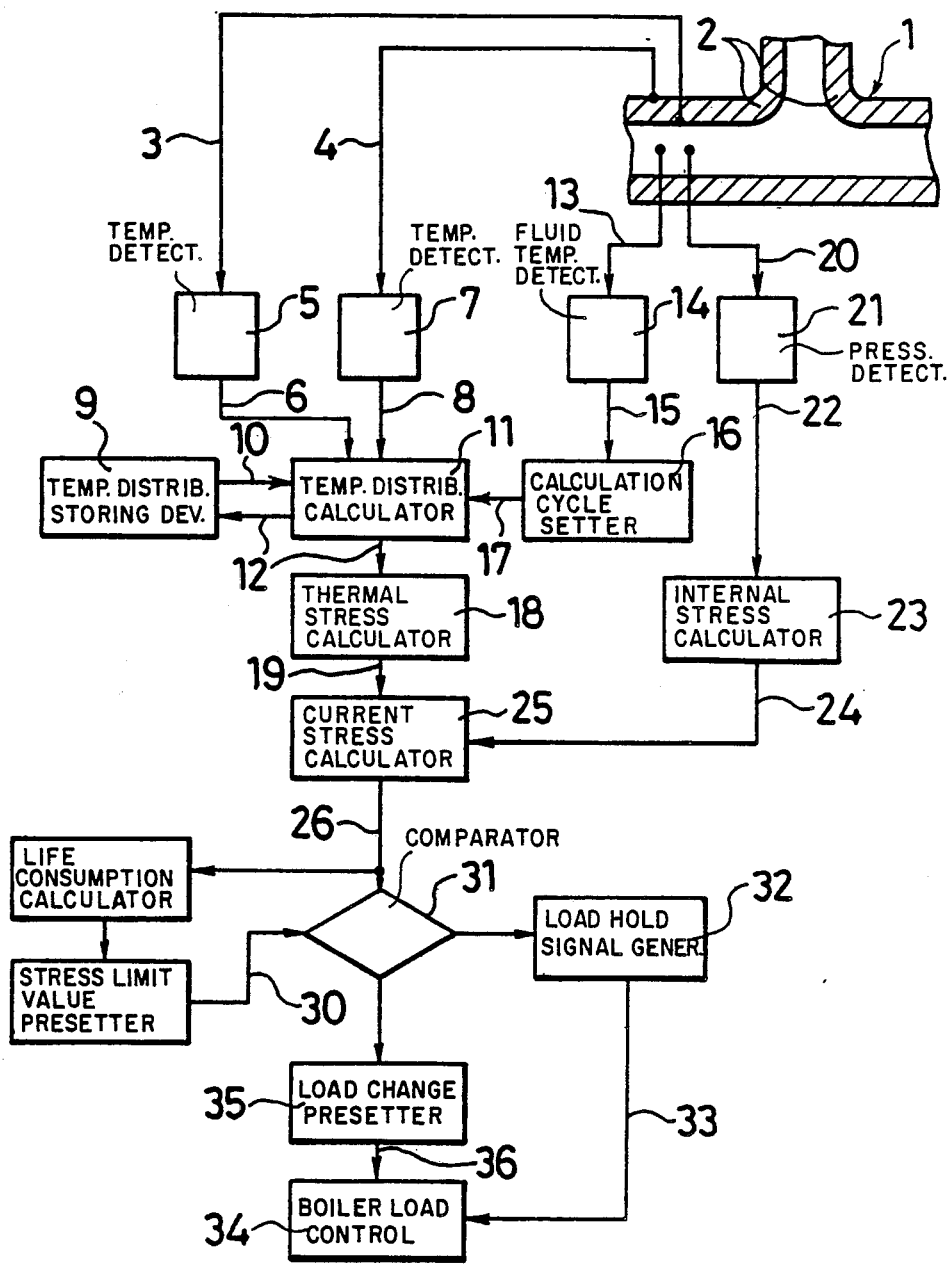
FIG. 1 is a schematic flow chart of the system for measuring thermal stress of a boiler embodying the present invention.

Firstly, description will be given of the outline of the system for estimating the thermal stress in a boiler with reference to FIG. 1.

As a typical example of a thermal stress monitoring point of a boiler, a nozzle corner portion 2 of a header 1 of a superheater will be described by way of an example.

This header 1 has a thick wall, and is used in conditions of high temperature close to 550° C. A difference in temperature between the inner and the outer surfaces of the header 1 occurs in accordance with changes in the fluid temperature and in the flowrate in the header 1 at the time of load changes such as start, stop or like operations. Particularly, the nozzle corner portion 2, being complicated in construction, has a complicated distribution of generated stress that is high in value. The nozzle corner portion 2 is a portion where the thermal stress is generated most notably.

Furthermore, the pressure of the internal fluid at the time of the steady operation amounts to as high as 255 Kg/cm$^2$, where the life consumption due to the internal pressure stress is also high.

In order to estimate the thermal stress at the monitoring points of the boiler the metal temperature is first measured. Count values 3 and 4 are provided from the inner surface and the outer surface of the header 1 respectively. A measured value 6 of the metal inner surface temperature is detected by a metal inner surface temperature detector 5, and a measured value 8 of the metal outer surface temperature is detected by a metal outer surface temperature detector 7. A calculated value 12 of the distribution of temperature in the direction of the metal thickness is calculated by a temperature distribution calculator 11 on the basis of the both measured values 6, 8 and a temperature distribution stored value 10 from a temperature distribution storing device 9.

On the other hand, in order to preset a calculation cycle for estimating the generated stress a fluid temperature is first measured from a count value 13 that is detected at the interior of the header 1. A fluid temperature measured value 15 is provided by a fluid temperature detector 14 that receives count value 13. In a calculation cycle setter 16, a rate of change in the fluid temperature is obtained on the basis of the fluid temperature measured values 15. This rate of change in the fluid temperature is compared with predetermined ranges of the change rate of the fluid temperature, and classified. A calculation cycle preset value 17 is then preset, which corresponds to the range of the plurality of rates of change in the fluid temperature.

In this case, the calculated value 12 of the distribution of temperature in the direction of the metal thickness is stored in the temperature distribution storing device 9, and added to a thermal stress calculator 18 to obtain a thermal stress calculated value 19.

On the other hand, a pressure measured count value 20 is detected from the header 1 by a pressure detector 21, and an internal stress calculated value 24 is obtained by an internal stress calculator 23 from a steam pressure measured count value 22 detected by the pressure detector 21.

In a current stress calculator 25, an internal pressure stress calculated value 24 obtained on the basis of a steam pressure measured count value 22 detected by the pressure detector 21 is added to the thermal stress calculated value 19 obtained on the basis of the calculated value 12 of the distribution of temperature in the direction of the metal thickness, to thereby calculate a current stress obtain value 26.

On the other hand, in a life consumption calculator 27, a life consumption calculated value 28 due to fatique and creep is calculated on the basis of the current stress caluculated value 26. In a stress limit value presetter 29, a life consumption calculated value 28 in the practical operation is subtracted from a life allotment which has been determined at the time of planning with every monitoring point and with every operation mode, to thereby calculate a remaining life. Further, from the remaining life and remaining operation cycles, an allowable life consumption per operation mode for the future is determined, and stress to be generated, which is expected to bring about this life consumption, is preset as a stress limit preset value 30 of the header 1.

This stress limit preset value 30 from the stress limit preset value setter 29 is adapted to be renewed with every desired cycle of the start or stop.

Next, the current stress calculated value 26 is compared with the stress limit preset value 30 in a comparator 31, whereby, when the current stress calculated value 26 exceeds the stress limit preset value 30, a load hold signal 33 is generated in a load hold signal generator 32 and delivered to a boiler load controller 34.

On the other hand, when the current stress calculated value 26 is lower than the stress limit preset value 30, an optimal rate of change in load (rate of change in fuel and rate of change in pressure) of the boiler, is selected from several predetermined load load changing rates by a load change rate presetter 35 as a load change rate preset value 36.

As described above, in the system for estimating thermal stress according to the present invention, the nozzle corner portion 2 is noted as being a stress concentrated portion in the header 1 in FIG. 1, and the generated stress and the life consumption are monitored. In this case, the fluid temperature measured value 15 is detected by the fluid temperature detector 14 in predetermined sample cycles.

Figure 3:
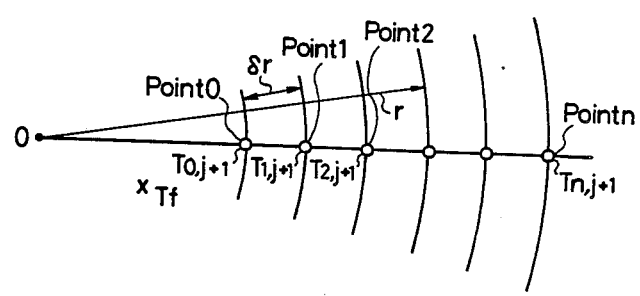
FIG. 3 is an enlarged sectional view taken along the line X—X in FIG. 2, showing a cylindrical model for calculating the distribution of temperature.

The following gives the detailed description of the temperature distribution calculator 11 in FIG. 11 and FIG. 3.

Figure 2:
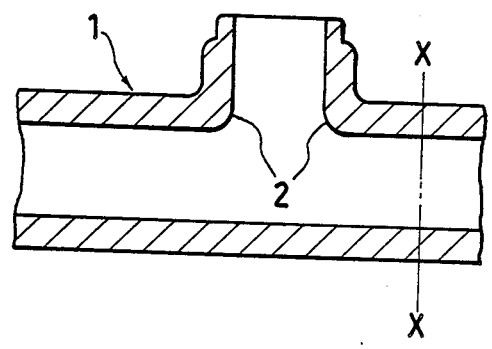
FIG. 2 is a view showing the header of FIG. 1 in detail.

FIG. 3 is an enlarged sectional view taken along the line X—X in FIG. 2, showning a cylindrical model for calculating the distribution of temperature.

Thermal stress in a cylindrical portion is obtained from the distribution of temperature in the direction of the thickness of the cylindrical portion. The distribution of temperature is obtained such that, in the following equation (1) of heat transmission with cylindrical coordinates, the cylindrical portion is divided by n elements, which are cylinders concentric with one another, with grid points being disposed at regular intervals, and the equation (1) is solved by the finite difference method.

$$\frac{1}{\alpha} \frac{\partial T}{\partial t} = \frac{\partial^2 T}{\partial \gamma^2} + \frac{1}{\gamma} \frac{\partial T}{\partial \gamma} \tag{1}$$

where $\alpha$: thermal conductivity of metal,
T: metal temperature at the coordinate point $(\gamma, \theta, Z)$,
t: time, and
$\gamma$: a distance from the center of the cylinder.

A difference equation is represented by an equation (2), and equations at the respective grid points are obtainable as equations (3).

$$\frac{1}{\alpha} \frac{T_{i,j+1} - T_{i,j}}{\delta t} = \tag{2}$$

$$\frac{1}{2} \left( \frac{T_{i+1,j+1} - 2T_{i,j+1} + T_{i-1,j+1}}{(\delta\gamma)^2} + \frac{T_{i+1,j} - 2T_{i,j} + T_{i-1,j}}{(\delta\gamma)^2} \right) +$$

$$\frac{1}{2\gamma} \left( \frac{T_{i+1,j+1} - T_{i-1,j+1}}{2\delta\gamma} + \frac{T_{i+1,j} - T_{i-1,j}}{2\delta\gamma} \right)$$

For the grid point 1:

$$-A \cdot T_{i,j+1} + T_{2,j+1} = -B \cdot (T_{0,j} + T_{0,j+1}) + C \cdot T_{i,j} - T_{2,j} \ldots \tag{3}$$

For the grid point 2:

$$B \cdot T_{i,j+1} - A \cdot T_{2,j+1} + T_{3,j+1} = -B \cdot T_{i,j} + C \cdot T_{2,j} - T_{3,j} \ldots \tag{3}$$

For the grid point 3:

$$B \cdot T_{2,j+1} - A \cdot T_{3,j+1} + T_{4,j+1} = -B \cdot T_{2,j} + C \cdot T_{3,j} - T_{4,j} \ldots \tag{3}$$

For the grid point (n−1):

$$-\frac{B}{A} \cdot T_{n-2,j+1} + T_{n-1,j+1} = \frac{B}{A} \cdot T_{n-2,j} - \frac{C}{A} \cdot \tag{3}$$

$$T_{n-1,j} + \frac{1}{A} (T_{n,j} + T_{n,j+1})$$

Here, $$A = \left( \frac{1}{(\delta\gamma)^2} + \frac{1}{\alpha\delta tm} \right) / \frac{1}{2\delta\gamma} \left( \frac{1}{\delta\gamma} + \frac{1}{2\gamma} \right)$$

$$B = \left( \frac{1}{\delta\gamma} - \frac{1}{2\gamma} \right) / \left( \frac{1}{\delta\gamma} + \frac{1}{2\gamma} \right)$$

$$C = \left( \frac{1}{(\delta\gamma)^2} - \frac{1}{\alpha\delta tm} \right) / \frac{1}{2\delta\gamma} \left( \frac{1}{\delta\gamma} + \frac{1}{2\gamma} \right)$$

where
$T_{i,j}$: metal temperature
(i: grid point number,
j: time division number),
$T_{0,j}$: inner surface temperature of metal, measured valve 6 in FIG. 1.
$T_{n,j}$: outer surface temperature of metal, measured valve 8 in FIG. 1.
$\delta\gamma$: split width of plate thickness, and
$\delta t = \delta tm$: calculation cycle (sec.) (m=1−M).
A, B, C: time-independent coefficients of equation (3), but function of position r, split width $\delta r$ and time division $\delta tm$.

In equations (3), the right hand terms are composed only with known variables, which are $T_{N,j}$(N=1 to n−1) calculated in the previous calculation cycle, $T_{0,j}$ and $J_{n,j}$ measured in the previous cycle, and $T_{0,j+1}$ and $T_{n,j+1}$ measured in the current computation cycle.

The left hand of equation (3) is composed with unknown variables, $T_{N,j+1}$(N=1 to n−1) which mean the current temperature distribution on the grid points.

Equations (3) can be solved by the linear matrix calculation, because number of equations of equation (3) is as same as number of unknown quantities $T_{N,j+1}$ (N=1 to n−1). Boundary values $T_0$, j+1, $T_n$, j+1 are the temperatures of the inner and outer surfaces of the metal, and given by the metal inner surface temperature measured value 6 and the metal outer surface temperature measured value 8, respectively. In consequence, the calculated value 12 of the distribution of temperature in the metal thickness, i.e. $T_N$, j+1(N=0, 1, 2, ... n) is obtainable and calculable. The thermal stresses are clculated by thermal stress calculator 18 as follows. The thermal stresses in the three directions $\sigma rt$, $\sigma\theta t$ and $\sigma zt$ can be obtained through the following equations.

$$\sigma rt = \frac{E\alpha'}{1-\nu} \left\{ \frac{1}{b^2 - a^2} \left( 1 - \frac{a^2}{\gamma^2} \right) \int_a^b Tydy - \frac{1}{\gamma^2} \int_a^b Tydy \right\} \tag{4}$$

$$\sigma\theta t = \frac{E\alpha'}{1-\nu} \left\{ \frac{1}{b^2 - a^2} \left( 1 + \frac{a^2}{\gamma^2} \right) \int_a^b Tydy + \tag{5}$$

-continued $$\sigma_{zt} = \frac{E\alpha'}{1-\nu} \left\{ \frac{2}{b^2-a^2} \int_a^b Tydy - T \right\} \quad \frac{1}{y^2} \int_a^b Tydy - T \Bigg\} \quad (6)$$

where
- $\sigma_{rt}$: thermal stress in the radial direction,
- E: Young's modutus of elasticity,
- $\sigma\theta t$: thermal stress in the circumferential direction,
- $\alpha'$: coefficient of thermal expansion,
- $\sigma_{zt}$: thermal stress in the axial direction, and
- $\nu$: Poisson's ratio.

Next, the stresses in the three directions due to the internal pressure are obtainable through the following equations.

$$\sigma_{rp} = -P \quad (7)$$

$$\sigma\theta p = \frac{P \cdot Di}{2t} + \frac{P}{2} \quad (8)$$

$$\sigma_{zp} = \frac{P \cdot Di}{2t} + \frac{P}{2} \quad (9)$$

where
- $\sigma_{rp}$: stress of inner pressure in the radial direction,
- P: inner pressure corresponding to measured value 22,
- $\sigma\theta p$: stress of inner pressure in the circumferential direction,
- Di: inner diameter,
- $\sigma_{zp}$: inner surface stress in the radial direction, and
- t: cylinder thickness.

The above-mentioned equations (4) through (9) represent stresses generated in a cylindrical portion of a boiler header, which is calculated by current stress calculator 25. The stress generated in the stress concentrated portion such as the nozzle corner portion 2 is obtained by multiplying the stress generated in the cylindrical portion by a stress concentration factor. In consequence, the stresses in the three directions of the current stress calculated value 26 generated in the nozzle corner portion 2 are obtainable through the equations (10) to (12).

$$or = Krt \cdot ort + Krp \cdot orp \ldots \quad (10)$$

$$o\theta = K\theta t \cdot o\theta t + K\theta p \cdot o\theta p \ldots \quad (11)$$

$$oz = Kzt \cdot ozt + Kzp \cdot ozp \ldots \quad (12)$$

where
- Krt: radial thermal stress concentration factor,
- K$\theta$t: circumferential thermal stress concentration factor,
- Kzt: axial thermal stress concentration factor,
- Krp: radial internal pressure stress concentration factor,
- K$\theta$p: circumferential internal pressure stress concentration factor,
- Kzp: axial internal pressure stress concentration factor,
- or: radial total stress,
- o$\theta$: circumferential total stress, and
- oz: axial total stress.

The distribution of temperature in the direction of the thickness in the pressure part portion of the boiler in the prior art has heretofore been estimated by assuming the distribution of temperature through a linear approximation from the metal inner and outer surface measured values 6 and 8. In this case, if the actual distribution of temperature in the direction of metal thickness is of a curve, the estimating accuracy of the generated stress is lowered.

Now, when the system for estimating the thermal stress according to the present invention is used, a partial differential equation is solved, and calculations can be made at suitable intervals of time to seek the distributions of temperature at the respective grid points, whereby the accuracy thereof is higher than the conventional system, so that the generated stress can be reliably determined.

Furthermore, the thermal stress measuring calculations can be performed in real time operation within a temperature measuring interval, during which changes in temperature can be satisfactorily grasped, so that changes in the distribution of temperature can be determined momentarily, thereby enabling estimation of the generated stress with high accuracy.

In the following case, the boundary condition of the inner surface of the metal (metal inner surface temperatures) is determined from the coefficient of heat-transfer of the fluid in contact with the interior to the metal. First, a steam temperature measured value is detected by a steam temperature detector, a steam flowrate measured value is detected by a steam flowrate detector and the steam pressure measured value is detected by the pressure detector. On the basis of these values, the coefficient of heat-transfer from the steam to the metal is calculated in a heat-transfer coefficient calculator. Subsequently, the distribution of temperature of the metal may be obtained by the temperature distribution calculator. The equation (1) of the heat conduction of the cylinder is solved, with the following equation being used as the boundary condition for the inner surface of the metal. Thus, the distribution of temperature of the metal is obtainable.

$$-\lambda \partial \frac{T}{\partial r} = h(T_f - T_0) \quad (13)$$

where
- $T_f$: fluid temperature, and
- $T_0$: inner surface temperature of metal.

In the embodiment of the present invention as shown in FIG. 1, an estimated calculation method of is used to determine the distribution of the temperature, the calculation has been made on the basis of the measured values of the inner and outer surface temperatures of the metal. However, as for the portions where high accuracy of estimation of the generated stress is not required, the generated stress may be sougnt from the temperature, pressure, and flowrate of the fluid and the temperature of the outer surface of the metal.

In the embodiment shown in FIG. 1, only one thermal stress monitoring point has been used, however, in practice, a plurality of such monitoring points as described above are provided, thus determining a method of operating the boiler, wherein all the requirements are satisfied.

Figure 4:
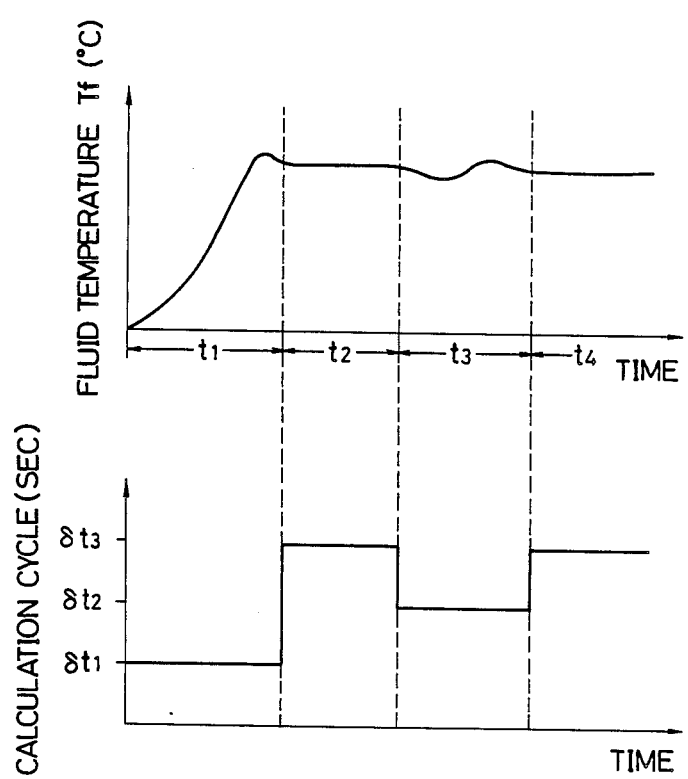
FIG. 4 is a characteristic curve diagram showing the correlation between the fluid temperature and the calculation cycle.

Description will hereunder be given of the method of presetting the calculation cycle preset value 17 with reference to FIG. 4. FIG. 4 shows an example of changes in the fluid temperature from the start of the boiler to the steady operation. FIG. 4 shows that, at the time $t_1$ of a change in the load such as the start of the boiler where fluctuations in the fluid temperature are large, a calculation cycle $\delta t_1$ is preset, at the times of $t_2$ and $t_4$ of the steady operation where fluctuations in the fluid temperature are small, a calculation cycle $\delta t_2$ is preset, and at the time $t_3$ of an intermediate change in the fluid temperature, a calculation cycle $\delta t_2$ is preset. In the practical system, an absolute value $\Delta|T_f|$ of the rate of change in the temperature is obtained by use of the fluid temperature measured values 15 for detecting the fluid temperature at predetermined sample cycles, and, in the calculation cycle setter 16, the calculation cycle preset value 17 corresponding to the absolute value $\Delta|T_f|$ is preset.

When this method is adopted, the calculation cycle for estimating the generated stress during the time period of monitoring the stress can be altered in accordance with the operating conditions of the boiler, whereby any useless calculation can be dispensed with, so that the load imposed upon the computer can be reduced. Furthermore, over all the time period of monitoring the stress, the generated stress can be estimated in the optimal calculation cycles, so that the load imposed upon the computer can be decreased. For example, in FIG. 4, at the time of the steady operation where fluctuations in the fluid temperature are small, the generated stress is estimated in the calculation cycle $\delta t_2$ or $\delta t_3$, and, at the time of the start of the boiler where the load is changed, the generated stress is estimated in the calculation cycles $\delta t_1$, whereby, at the time of the steady operation, the calculations should be made once for two cycles or three cycles of the calculation cycle $\delta t_1$, so that the load imposed upon the computer can be decreased to ½ or ⅓.

When the load of the computer is reduced as described above, the computer can be further utilized in performing calculations for other purposes of control or in adding a new function or functions, thus proving economical.

Since, in the predetermined calculation cycles, it is determined that the generated stress can be estimated with high accuracy under the full load condition of the boiler, useless calculations are made at the time of the steady operation, etc. of the boiler, whereby the excessive accuracy would be required. In consequence, according to the present invention, at the time of the load change such as the start or stop of the boiler where the fluid temperature fluctuates greatly, the calculation cycles are made short, while at the time of the steady operation, etc., where changes in the fluid temperature are small, the calculation cycles are made long, so that over the total time period of the stress monitoring, the generated stress can be estimated with uniform accuracy.

According to the present invention, on the basis of the fluid temperature measured value from the pressure-tight tube portion of the heating device such as the boiler, the distribution of temperature in the direction of the metal thickness can be measured with high accuracy and the generated stress can be reliably measured. Furthermore, there is provided the calculation cycle setter for presetting the calculation cycles on the basis of the fluid temperature measured values, whereby, at the time of the load change where the fluid temperature fluctuates greatly, the calculation cycles are made short, while, at the time of the steady operation where the fluctuations of the fluid temperature are small, the calculation cycles are made long, so that the calculation cycles for estimating the generated stress can be altered in accordance with the operating conditions of the heating device, and moreover, the generated stress can be measured at a value close to the actual state.

What is claimed is:

1. A system for measuring thermal stress of a pressure-tight tube having a metal portion and a fluid therein, comprising:
    means for measuring temperature of at least the outer surface of said tube;
    temperature distribution calculating means for calculating distribution of temperature at positions equidistantly arranged in a direction of the thickness of said tube on the basis of measured values including at least a measured value from said temperature measuring means of the outer surface temperature of a metal portion of said tube;
    thermal stress calculating means for calculating a thermal stress value of the metal portion of said tube on the basis of said calculated distribution of temperature;
    internal stress calculating means for calculating an internal pressure stress value in said tube obtained on the basis of a measured fluid pressure value provided by a pressure detector for measuring the pressure of the fluid in said tube; and
    current stress calculating means for adding said internal pressure stress calculated value and said thermal stress calculated value together to obtain a current stress calculated value.

2. A system for measuring thermal stress of a pressure-tight tube as set forth in claim 1, wherein said temperature measuring means includes means for measuring the temperatures of the inner and outer surfaces, respectively, of the metal portion of said tube such that said measured values include said measured inner and outer surface temperatures, respectively.

3. A system for measuring thermal stress of a pressure-tight tube as set forth in claim 1, wherein said measured values include measured values provided by means for measuring the temperature, pressure and flow rate of the fluid in said tube, and a measured value of the outer surface temperature of the metal portion of said tube provided by said temperature measuring means.

4. A system for measuring thermal stress of a pressure-tight tube as set forth in claim 1, wherein said pressure-tight tube is part of a boiler.

5. A system for measuring thermal stress of a pressure-tight tube having a metal portion and having a fluid therein according to a calculation cycle, comprising:
    means for measuring temperature of at least the other surface of said tube;
    temperature distribution calculating means for calculating distribution of temperature at positions equidistantly arranged in a direction of thickness of said tube on the basis of measured values including at least the measured value from said temperature measuring means of the outer surface temperature of the metal portion of said tube;
    thermal stress calculating means for calculating thermal stress of the metal portion of said tube on the basis of said calculated distribution of temperature;
    internal pressure stress calculating means for providing an internal pressure stress value obtained on the basis of the fluid pressure detected by a pressure detector in said tube; and current stress calculating means for adding said thermal stress calculated value and said internal pressure stress calculated value together to obtain a current stress calculated value;
a fluid temperature detector for providing measured values of fluid temperature in said tube; and
calculation cycle setter means for presetting the calculation cycle on the basis of said measured values of fluid temperature whereby said calculation cycles are made short when fluctuations in the measured values of the fluid temperature are large, and further whereby said calculation cycles are made long when fluctuations in the measured values of the fluid temperature are small.

6. A system for measuring thermal stress of a pressure-tight tube as set forth in claim 5, wherein said temperature measuring means include means for measuring the temperatures of the inner and outer surfaces of the metal of said tube, respectively such that such measured inner and outer surface values include said measured temperatures, respectively.

7. A system for measuring thermal stress of a pressure-tight tube as set forth in claim 5, wherein said measured values are measured values of the temperature, pressure and flow rate of the fluid in said tube, and a measured value of the outer surface temperature of the metal portion of said tube.

8. A system for measuring thermal stress of a pressure-tight tube as set forth in claim 5, wherein said pressure-tight tube is provided as part of a boiler.

9. A system for controlling the load of a boiler by measuring thermal stress of a pressure-tight tube having a metal portion heated by said boiler and having a fluid therein, comprising:
means for measuring temperature of at least the outer surface of said tube;
temperature distribution calculating means for calculating distribution of temperature at positions equidistantly arranged in a direction of the thickness of said tube on the basis of measured values including at least the mesured value from the temperature measuring means of the outer surface temperature of the metal portion of said tube;
thermal stress calculating means for calculating thermal stress of the metal portion of said tube on the basis of said calculated distribution of temperature;
internal stress calculating means for calculating an internal pressure stress value on the basis of fluid pressure values provided by a pressure detector in said tube; and current stress calculating means for adding said thermal stress calculated value and said internal pressure stress calculated value together to obtain a current stress calculated value;
stress limit preset value setting means for presetting a stress which is estimated to bring about an allowable life consumption of said tube per operation mode;
stress limit presetting means for providing a stress limit preset value for said tube; and
means for comparing said current stress calculated value to said stress limit preset value, load change rate presetting means for selecting and providing an optimal preset load change rate value from a plurality of preset value, load hold signal generating means for providing a load hold signal, and a controller for controlling the load of said boiler and for receiving said load hold signal and load change rate preset value; whereby, when the current stress calculated value exceeds the stress limit preset value, a load hold signal is generated and delivered to the controller, while when the current stress calculated value is lower than the stress limit preset value, an optimal load change rate value is selected and delivered to said controller from said load change rate presetter.

10. A system for controlling the load of a boiler by measuring thermal stress of a pressure-tight tube having a metal portion heated by said boiler and having a fluid therein, comprising:
means for measuring temperature of at least the outer surface of said tube;
temperature distribution calculating means for calculating distribution of temperature at positions equidistantly arranged in a direction of the thickness of said tube on the basis of measured values including at least the measured value from the temperature measuring means of the outer surface temperature of the metal portion of said tube;
thermal stress calculating means for calculating thermal stress of the metal portion of said tube on the basis of said calculated distribution of temperature;
internal stress calculating means for calculating an internal pressure stress value on the basis of the fluid pressure detected by a pressure detector in said tube; and
current stress calculating means for adding said thermal stress calculated value and said internal pressure stress calculated value together to obtain a current stress calculated value;
stress limit preset value setting means for presetting a stress which is estimated to bring about an allowable life consumption of said tube per operation mode;
stress limit presetting means for providing a stress limit preset value for said tube;
means for comparing said current stress calculated value to said stress limit preset value, load change rate presetting means for selecting and providing an optimal preset load change rate value from a plurality of preset valves, load hold signal generating means for providing a load hold signal, and a controller for controlling the load of said boiler and for receiving said load hold signal and load change rate preset value; whereby, when the current stress calculated valve exceeds the stress limit preset value, a load hold signal is generated and delivered to the controller, while when the current stress calculated value is lower than the stress limit preset value, an optimal load change rate value is delivered to said controller from said load change rate presetter; and
a calculation cycle setter for presetting the calculation cycle on the basis of said measured values of fluid temperature, whereby said calculation cycles are made short when fluctuations in the measured values of the fluid temperature are large, and further whereby said calculation cycles are made long when fluctuations in the measured values of the fluid tempeature are small.

* * * * *